(12) United States Patent
Liu et al.

(10) Patent No.: US 11,944,264 B2
(45) Date of Patent: Apr. 2, 2024

(54) CONFOCAL ENDOSCOPE WITH FIXING DEVICE

(71) Applicant: HAINAN UNIVERSITY, Hainan (CN)

(72) Inventors: Qian Liu, Hainan (CN); Ling Fu, Hainan (CN); Xiaoxiao Ma, Hainan (CN); Gang Zheng, Hainan (CN); Yu Feng, Hainan (CN)

(73) Assignee: HAINAN UNIVERSITY, Hainan (CN)

( * ) Notice: Subject to any disclaimer, the term of this patent is extended or adjusted under 35 U.S.C. 154(b) by 139 days.

(21) Appl. No.: 17/773,463

(22) PCT Filed: Jun. 22, 2021

(86) PCT No.: PCT/CN2021/101527
§ 371 (c)(1),
(2) Date: Apr. 29, 2022

(87) PCT Pub. No.: WO2021/259258
PCT Pub. Date: Dec. 30, 2021

(65) Prior Publication Data
US 2022/0369902 A1    Nov. 24, 2022

(30) Foreign Application Priority Data
Jun. 24, 2020   (CN) .......................... 202010590138.7

(51) Int. Cl.
*A61B 1/00*   (2006.01)
*A61B 1/005*  (2006.01)
*A61B 1/07*   (2006.01)

(52) U.S. Cl.
CPC ...... *A61B 1/00071* (2013.01); *A61B 1/00082* (2013.01); *A61B 1/00135* (2013.01);
(Continued)

(58) Field of Classification Search
CPC ............ A61B 1/00082; A61B 1/00135; A61B 1/00148
See application file for complete search history.

(56) References Cited

U.S. PATENT DOCUMENTS 3,746,003 A * 7/1973 Blake ................ A61M 25/1034
604/102.02
5,855,569 A * 1/1999 Komi ..................... A61B 10/04
604/103

(Continued)

FOREIGN PATENT DOCUMENTS

CN    101066204 A    11/2007
CN    201537130 U    8/2010
(Continued)

*Primary Examiner* — Matthew J Kasztejna
(74) *Attorney, Agent, or Firm* — RABIN & BERDO, P.C.

(57) ABSTRACT

The present invention relates to the technical field of endoscopes, and discloses a confocal endoscope with a fixing device. The confocal endoscope includes an insertion tube, a flexible tube, a plurality of airbag assemblies, and a pressure supply assembly, where the flexible tube is slidably sleeved on the insertion tube, a plurality of containing units are formed in an outer wall of the flexible tube in an axial direction and are distributed in the axial direction of the flexible tube at intervals, each containing unit includes a plurality of containing grooves evenly distributed in a circumferential direction of the flexible tube, and the outer wall of the flexible tube is concaved inwards to form the containing grooves; the airbag assemblies and the containing units are arranged in a one-to-one correspondence mode, each airbag assembly includes a plurality of elastic airbags, the elastic airbags and the containing grooves are arranged in a one-to-one correspondence mode, and the elastic airbags are connected to inner walls of the containing grooves; the pressure supply assembly is selectively communicated with the elastic airbags of one or more airbag assemblies and
(Continued)

configured to inject fluid media with certain pressure into the elastic airbags. According to the present invention, the insertion tube can be prevented from jittering.

19 Claims, 10 Drawing Sheets

(52) U.S. Cl.
CPC .......... *A61B 1/00148* (2022.02); *A61B 1/005* (2013.01); *A61B 1/07* (2013.01)

(56) References Cited

U.S. PATENT DOCUMENTS

| | | | |
|---|---|---|---|
| 2001/0020150 A1 | 9/2001 | Ravo | |
| 2008/0033246 A1* | 2/2008 | Matsui | A61B 1/00082 600/115 |
| 2008/0269559 A1 | 10/2008 | Miyamoto et al. | |
| 2008/0281155 A1* | 11/2008 | Fujikura | A61B 1/00082 600/115 |
| 2010/0121144 A1 | 5/2010 | Farhadi | |
| 2013/0027516 A1* | 1/2013 | Hart | A61B 5/0071 348/45 |
| 2018/0368665 A1 | 12/2018 | Rentschler et al. | |

FOREIGN PATENT DOCUMENTS

| | | |
|---|---|---|
| CN | 102205160 A | 10/2011 |
| CN | 111920366 A | 11/2020 |
| JP | 2004-097391 A | 4/2004 |
| JP | 2005-270335 A | 10/2005 |
| JP | 2005-279072 A | 10/2005 |

\* cited by examiner

CONFOCAL ENDOSCOPE WITH FIXING DEVICE

TECHNICAL FIELD

The present invention relates to the technical field of endoscopes, and in particular, to a confocal endoscope with a fixing device.

BACKGROUND

A confocal microendoscope comes from confocal microscopes commonly used in laboratories, and applies the principle of confocal microscopes used on traditional laboratory desktops to endoscopy technology. The confocal endoscope is widely used in the examination because of its excellent three-dimensional layer suction ability and high resolution. The confocal endoscope generally includes an insertion portion, a control portion, and an imaging portion. The insertion portion includes an insertion tube, a lens, a fiber optic bundle, other pipelines, etc., The lens is disposed at one end of the insertion tube, and the fiber optic bundle is built into the insertion tube. The control portion completes a series of control actions through its pipeline, and the imaging portion is configured to display an image of internal tissues of a human body. The effective pixels of a pattern of such an endoscope depend on the number of fiber cores of an image-transmitting fiber optic bundle, and the imaging speed is 3 to 24 frames per second. When the insertion portion of the endoscope jitters, the image becomes blurred.

SUMMARY

An objective of the present invention is to overcome the above technical deficiencies, to provide a confocal endoscope with a fixing device for solving the technical problem in the prior art of jitter in the use of the confocal endoscope.

To achieve the foregoing technical objective, the technical solution of the present invention provides a confocal endoscope with a fixing device, including:

an insertion tube;

a flexible tube, slidably sleeved outside the insertion tube, where a plurality of containing units are formed in an outer wall of the flexible tube in an axial direction and are distributed in the axial direction of the flexible tube at intervals, each containing unit includes a plurality of containing grooves evenly distributed in a circumferential direction of the flexible tube, and the outer wall of the flexible tube is concaved inwards to form the containing grooves;

a plurality of airbag assemblies, where the airbag assemblies and the containing units are arranged in a one-to-one correspondence mode, each airbag assembly includes a plurality of elastic airbags, the elastic airbags and the containing grooves are arranged in a one-to-one correspondence mode, and the elastic airbags are connected to inner walls of the containing grooves; and a pressure supply assembly, selectively communicated with the elastic airbags of one or more airbag assemblies and configured to inject fluid media into the elastic airbags; where the elastic airbags are bulged to limit the flexible tube and restrain the insertion tube;

where a plurality of fixing holes are formed on the flexible tube and are arranged in the axial direction of the flexible tube; inner walls of the containing grooves are concaved inwards to form first communicating holes; the first communicating holes are communicated with the fixing holes, and the elastic airbags are communicated with the first communicating holes; the pressure supply assembly includes a plurality of conveying elements and pressure supply elements; the conveying elements and the fixing holes are arranged in a one-to-one correspondence mode; each conveying element includes a conveying tube and a sealing portion; the conveying tube is slidably inserted in the fixing hole and is sealedly connected to an inner wall of the fixing hole; second communicating holes opposite to the first communicating holes are formed on the conveying tube; the second communicating holes and the first communicating holes are arranged in a one-to-one correspondence mode; the sealing portion selectively seals some of the second communicating holes; and the pressure supply element is communicated with each conveying tube and configured to inject fluid media into the conveying tube.

Compared with the prior art, the beneficial effects of the present invention include: when it is necessary to detect the stomach and intestines of the human body through a confocal endoscope, a detected site is roughly preset first, an appropriate insertion distance is selected, and then the number of elastic airbags to be set is selected as required. Then the insertion tube, the airbags and the flexible tube are inserted into a site to be detected of the human body. When a lens on the insertion tube is about to reach a predetermined point, the pressure supply assembly is activated, and the pressure supply assembly injects fluid media into the elastic airbags. Under the pressure of the fluid media, the elastic airbags are continuously stretched, so that the elastic airbags are abutted against the human body. In this case, under the action of the elastic airbags, the elastic airbags limit the flexible tube and move the insertion tube, and the insertion tube slides relative to the flexible tube. Because the existence of the flexible tube and the elastic airbags may restrain the insertion tube, the jitter of the insertion tube is reduced or avoided, and the blurring of an image transmitted from the fiber optic bundle caused by the jitter of the insertion tube is avoided.

DETAILED DESCRIPTION

To make the objective, technical solution, and advantages of the present invention clearer, the following further describes the present invention in detail with reference to the accompanying drawings and embodiments. It should be understood that the specific embodiments described herein are merely used for explaining the present invention but are not intended to limit the present invention.

The present invention provides a confocal endoscope with a fixing device, as shown in FIG. 1 to FIG. 11, including an insertion tube 1, a flexible tube 2, a plurality of airbag assemblies 3 and a pressure supply assembly 4. The insertion tube 1 is the prior art, and thus is not elaborated.

The flexible tube 2 is slidably sleeved on the insertion tube 1. A plurality of containing units 21 are formed in an outer wall of the flexible tube 2 in an axial direction and distributed in the axial direction of the flexible tube 2 at intervals. Each containing unit 21 includes a plurality of containing grooves 211 evenly distributed in a circumferential direction of the flexible tube 2, and the outer wall of the flexible tube 2 is concaved inwards to form the containing grooves 211.

A certain amount of force is required between the flexible tube 2 and the insertion tube 1 to slide.

The flexible tube 2 is made of various flexible materials, and the specific material of the flexible tube 2 is medical silica gel, but the material of the flexible tube 2 is not limited thereto.

The airbag assemblies 3 and the containing units are arranged in a one-to-one correspondence mode. Each airbag assembly 3 includes a plurality of elastic airbags 31. The elastic airbags 31 and the containing grooves are arranged in a one-to-one correspondence mode. The elastic airbags 31 are connected to inner walls of the containing grooves. When the elastic airbags 31 are not filled with substances, the elastic airbags 31 are located in the containing grooves under the action of own elastic force.

The number and spacing of the airbag assemblies 3 and the containing units may be set as required.

The number of the containing grooves in each containing unit and the number of the elastic airbags 31 in each airbag assembly 3 may be three, four, five, etc. Specifically, the number of the containing grooves in each containing unit and the number of elastic airbags 31 in each airbag assembly 3 are four, but the number of the containing grooves in each containing unit and the number of elastic airbags 31 in each airbag assembly 3 are not limited thereto.

The pressure supply assembly 4 is selectively communicated with the elastic airbags 31 of one or more airbag assemblies 3 and configured to inject fluid media with certain pressure into the elastic airbags 31.

The elastic airbags 31 and the pressure supply assembly 4 may be connected through a pipeline located outside the flexible tube 2, or a communicated pipeline may be provided in the flexible tube 2. Specifically, a plurality of fixing holes 22 are formed on the flexible tube 2. The fixing holes 22 are arranged along the axial direction of the flexible tube 2, the inner wall of each containing groove is concaved inwards to form a first communicating hole 231. The first communicating hole 231 is communicated with a certain fixing hole 22, and the elastic airbag 31 is communicated with the first communicating hole 231. The pressure supply assembly 4 includes a plurality of conveying elements 41 and pressure supplying elements 42. The conveying elements 41 and the fixing holes 22 are arranged in a one-to-one correspondence mode.

The number of the fixing holes and the conveying elements 41 may be three, four, five, etc. Specifically, the number of the fixing holes and the conveying elements 41 is four, and the four conveying elements 41 are evenly distributed along the circumferential direction of the conveying tube 411.

Specifically, the other end of the flexible tube 2 is concaved inwards to form the fixing hole, and the fixing hole is a blind hole.

Specifically, the side of the elastic airbag 31 close to the bottom of the containing groove is fit to the inner wall of the bottom of the containing groove. Fourth communicating holes opposite to the first communicating holes are formed on the elastic airbag 31. The fourth communicating holes are communicated with the first communicating holes.

Each conveying element 41 includes a conveying tube 411 and a sealing portion 412. The conveying tube 411 is slidably inserted in the fixing hole and is sealedly connected to an inner wall of the fixing hole. Second communicating holes 4111 opposite to the first communicating holes are formed on the conveying tube 411. The second communicating holes 4111 and the first communicating holes are arranged in a one-to-one correspondence mode. The sealing portion 412 is configured to selectively seal some of the second communicating holes 4111. The pressure supply element 42 is communicated with each conveying tube 411 and configured to inject fluid media with certain pressure into the conveying tube 411.

The fluid medium may be gas or liquid. When the fluid medium is gas, the pressure supply element 42 is an air pump. When the fluid medium is liquid, the pressure supply element 42 is a water pump. In the present application, the fluid medium used by the pressure supply element 42 is gas, the pressure supply element 42 is an air pump, and an air outlet end of the air pump is communicated with the other end of the conveying tube 411, but the types of the fluid media and the pressure supply element 42 are not limited thereto.

A plurality of annular grooves 4112 are formed on the conveying tube 411 and are distributed in an axial direction of the conveying tube 411 at intervals. The annular grooves 4112 are provided at both sides of each second communicating hole. Each conveying element 411 further includes a plurality of seal rings 413. The seal rings 413 and the annular grooves 4112 are arranged in a one-to-one correspondence mode. Inner races of the seal rings 413 are matingly inserted in the annular grooves 4112, and outer races are slidably abutted against the inner walls of the fixing holes and sealedly connected to the inner walls of the fixing holes.

The number and spacing of the annular grooves and the second communicating holes may be set as required.

Specifically, the interior of the conveying tube 411 is hollow, one end is closed, and the other end is open, and a closed end of the conveying tube 411 is slidably inserted in the fixing hole.

The space between the conveying tube 411 and the inner wall of the fixing hole is sealed by providing the seal rings 413. When the conveying tube 411 slides relative to the fixing hole, a gap between the inner wall of the fixing hole and the outer wall of the conveying tube 411 is avoided.

Specifically, the cross section of the annular groove is triangular, and the seal ring 413 includes a first ring body 4131 and a second ring body 4132. The cross section of the first ring body 4131 is triangular, an inner race of the first ring body 4131 is matingly embedded in the annular groove, the second ring body 4132 and the first ring body 4131 are coaxially arranged, and an inner race of the second ring body 4132 is connected to an outer race of the first ring body 4131, and the second ring body 4132 and the first ring body 4131 are integrally formed.

By arranging the annular groove with a triangular cross section and the first ring body 4131, the seal ring 413 may be prevented from sliding relative to the annular groove in the axial direction of the conveying tube 411.

The sealing portion 412 includes a plurality of seal cartridges 4121. The seal cartridges 4121 and the second communicating holes are arranged in a one-to-one correspondence mode. The seal cartridges 4121 are rotatably sleeved on the conveying tube 411 and sealedly connected to an outer wall of the conveying tube 411. Two ends of each seal cartridge 4121 are abutted against two adjacent seal rings 413, respectively. Third communicating holes 41211 opposite to the second communicating holes are formed on the seal cartridge 4121.

Furthermore, an outer diameter of the seal cartridge 4121 is smaller than that of the seal ring 413.

By designing the outer diameter of the seal cartridge 4121 to be smaller than that of the seal ring 413, when the conveying tube 411 slides in the fixing hole, the seal cartridge 4121 is not in contact with the inner wall of the fixing hole, so that the resistance of the conveying tube 411 relative to the fixed hole may be reduced.

Furthermore, each conveying element 41 also includes a branch tube 414 and a cover body 415. One end of the branch tube 414 is communicated with the other end of the conveying tube 411. External threads are provided on an outer wall of the other end of the branch tube 414 along the axial direction. The inner wall of the cover body 415 is hollow and one end is open. External threads are provided on the inner wall of the open end of the cover body 415 along the axial direction. The open end of the cover body 415 is threadedly connected to the other end of the branch tube 414.

The pressure supply element 42 is communicated with each conveying tube 411 through a pipeline, and each conveying element 41 further includes a valve 416. The valve 416 is disposed on the conveying tube 411 for controlling communication and closing of the conveying tube 411.

Furthermore, each conveying element 41 further includes an air pressure gauge 417. The air pressure gauge 417 is disposed at the other end of the conveying tube 411 for detecting the air pressure in the conveying tube 411.

Figure 1:
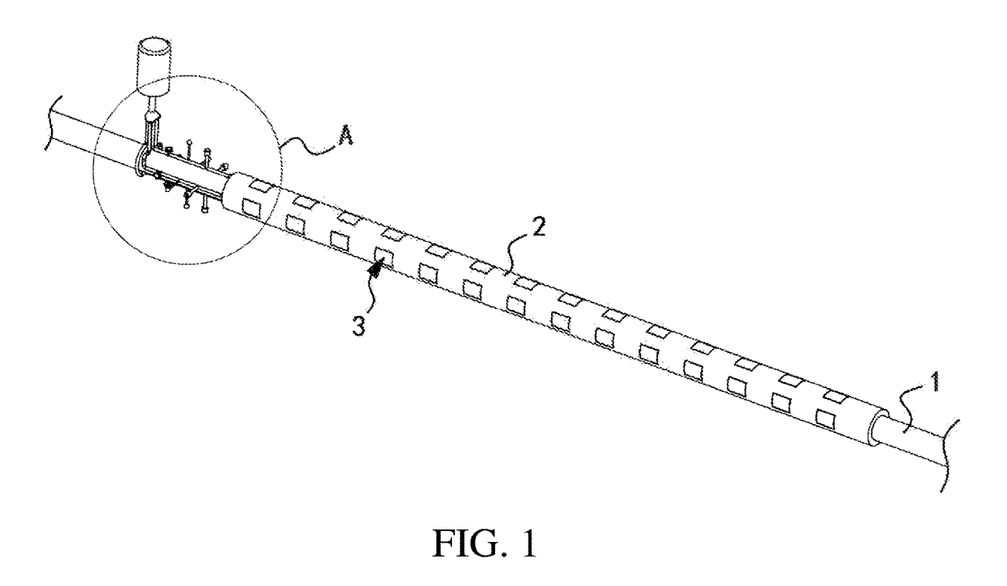
FIG. 1 is a schematic three-dimensional diagram of the present invention.
Figure 2:
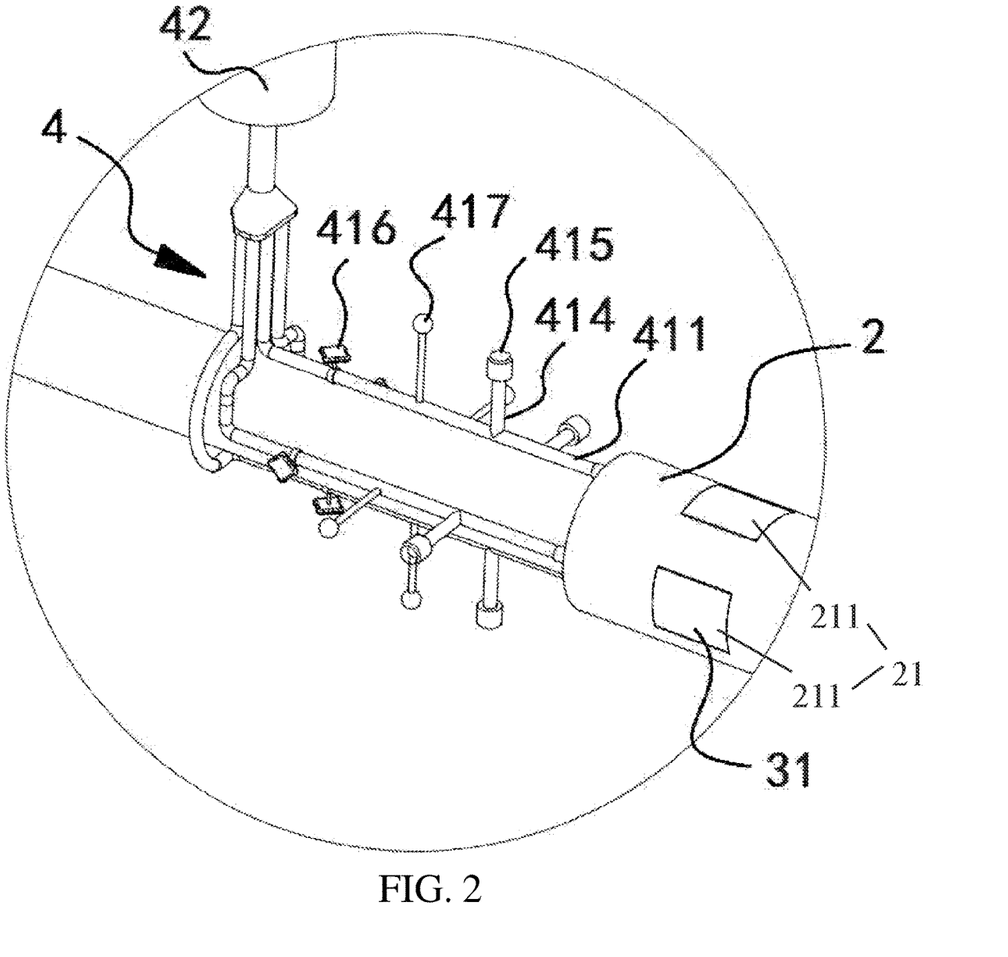
FIG. 2 is a partial enlarged diagram of part A in FIG. 1.
Figure 3:
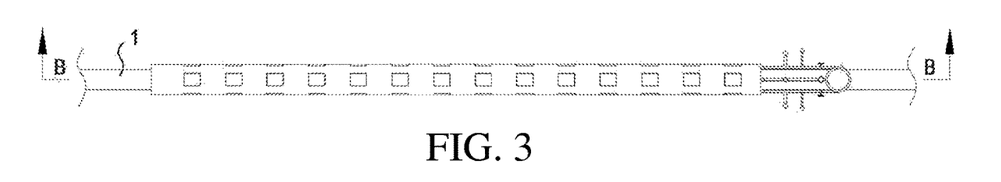
FIG. 3 is a schematic structural diagram of the present invention.
Figure 4:
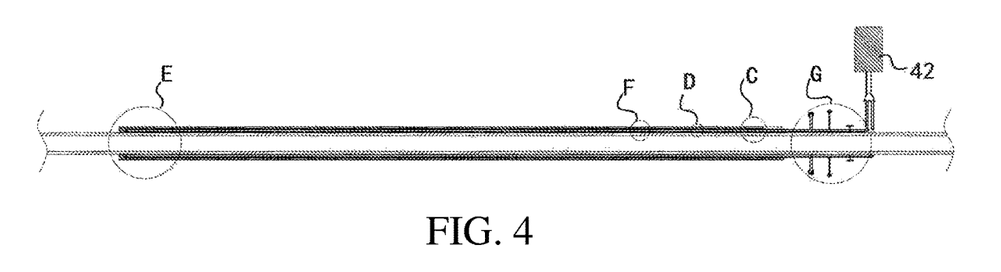
FIG. 4 is a sectional view along line B-B in FIG. 3.
Figure 5:
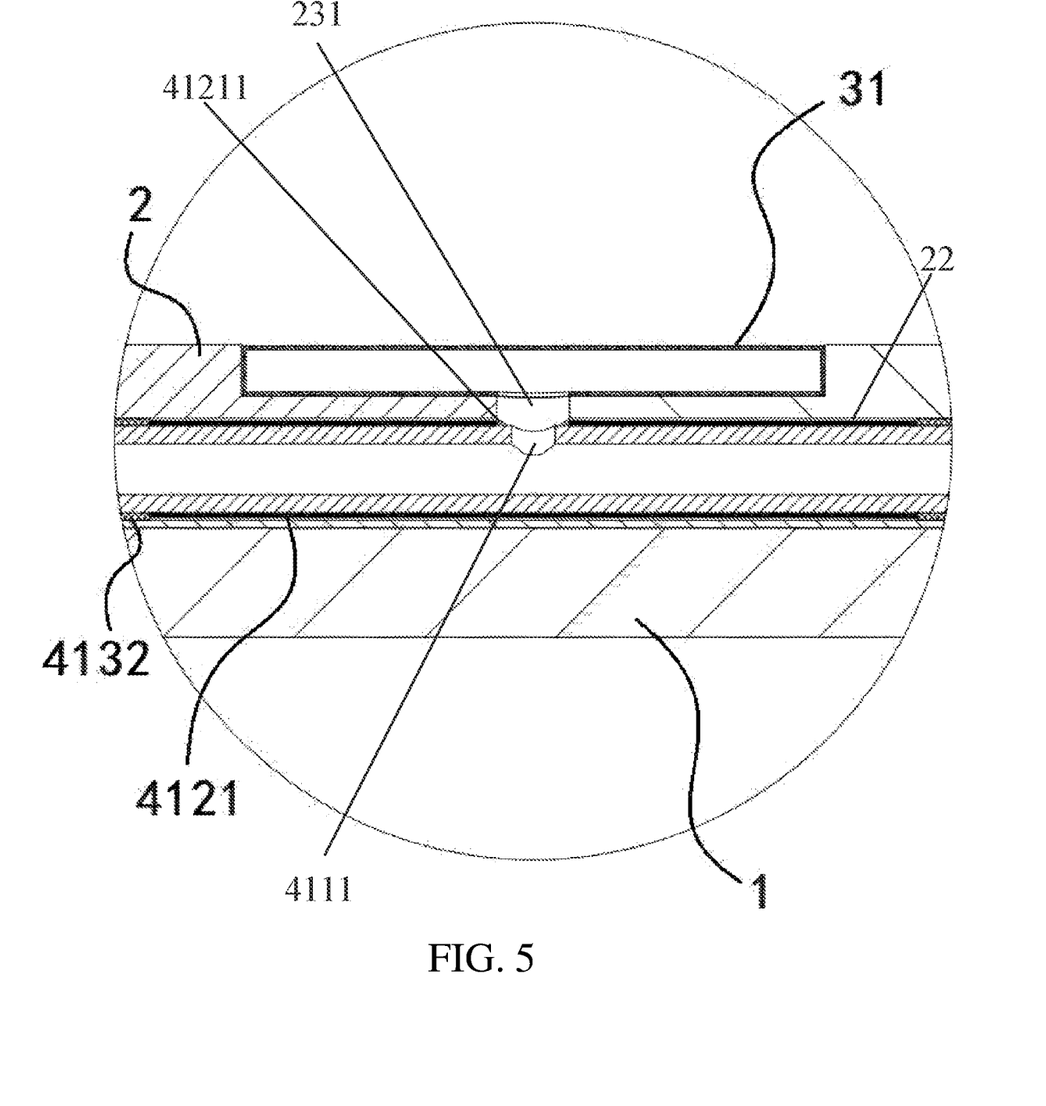
FIG. 5 is a partial enlarged diagram of part C in FIG. 4.
Figure 6:
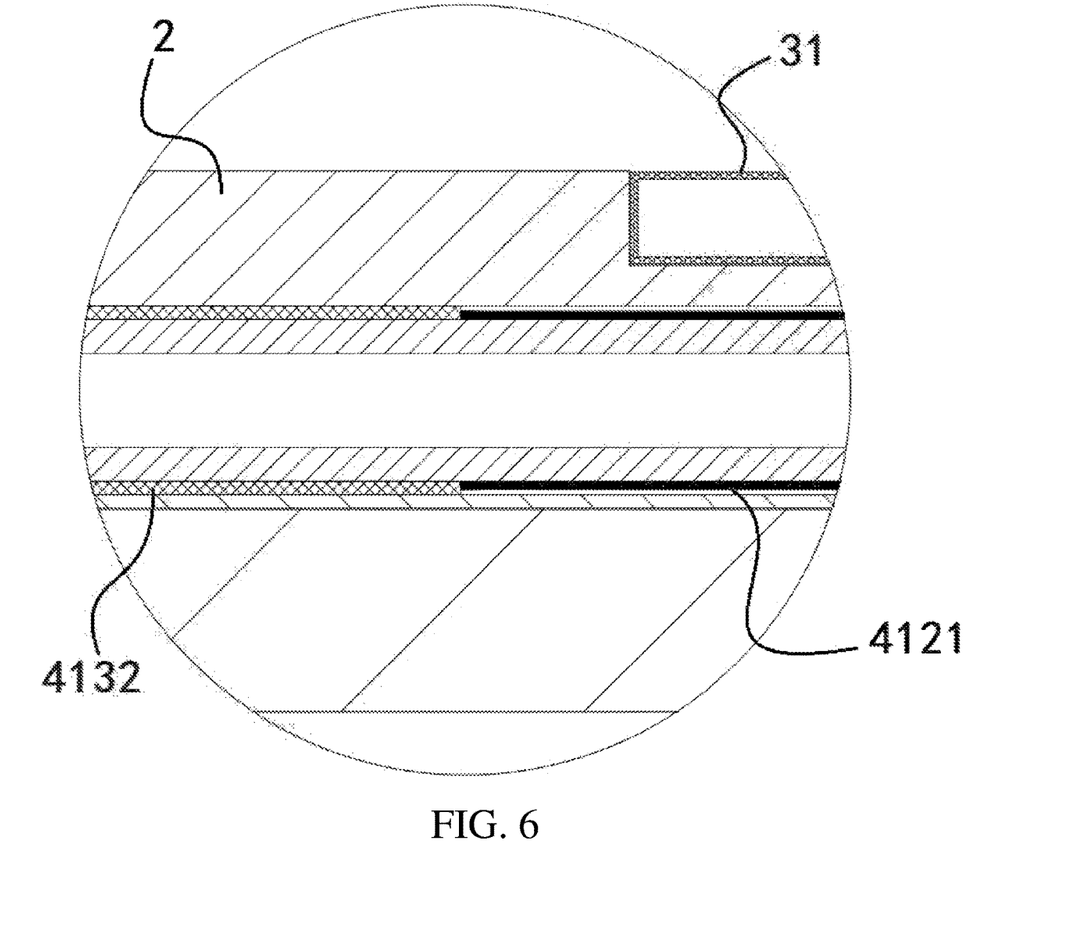
FIG. 6 is a partial enlarged diagram of part D in FIG. 4.
Figure 7:
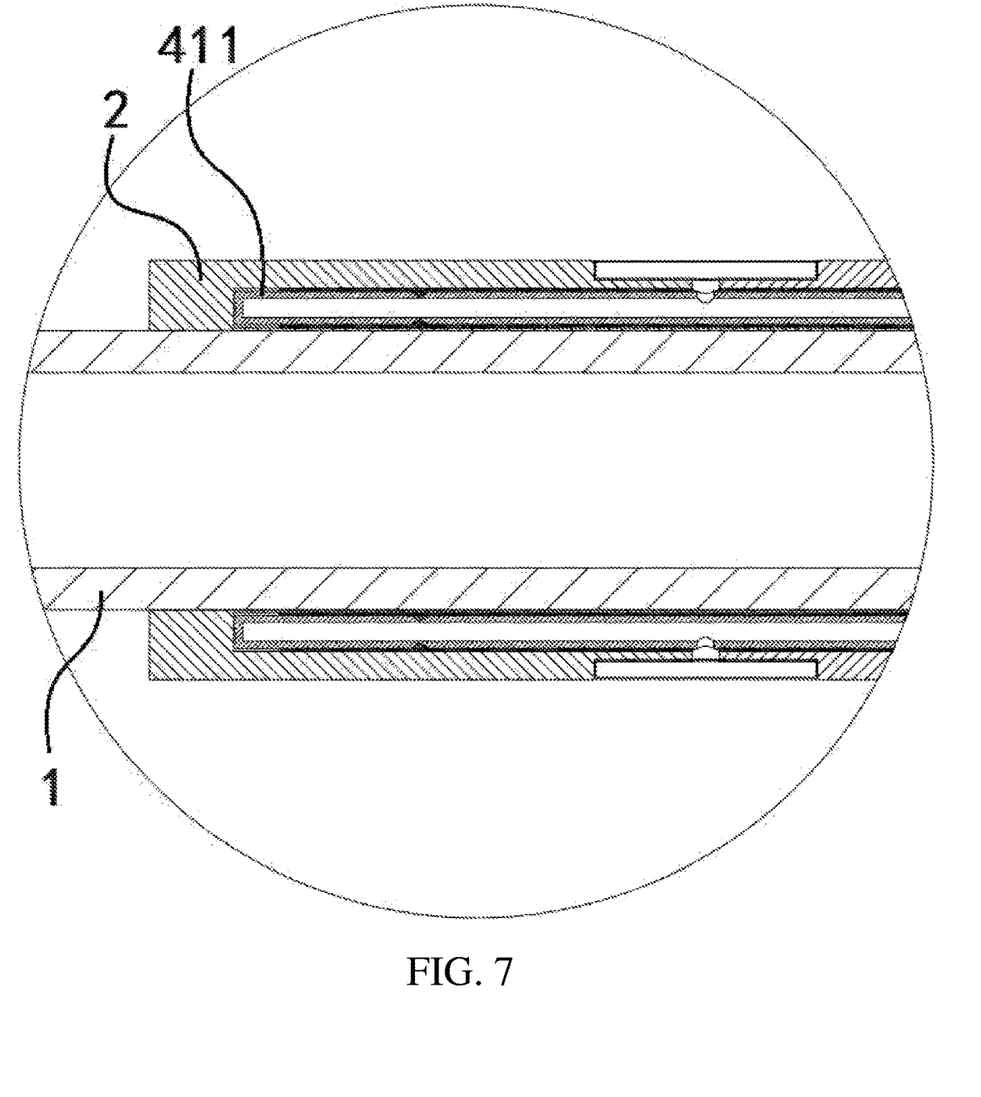
FIG. 7 is a partial enlarged diagram of part E in FIG. 4.
Figure 8:
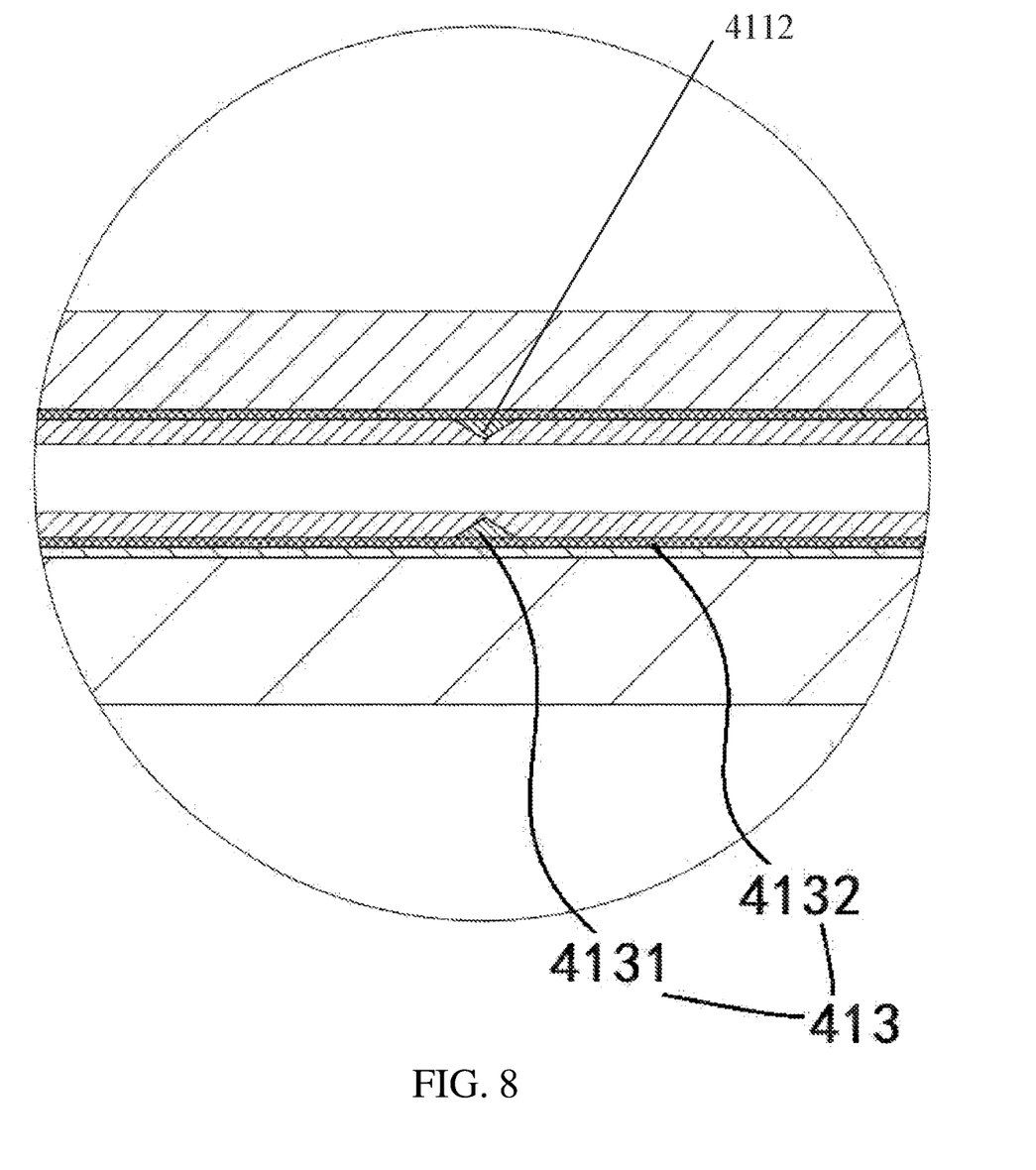
FIG. 8 is a partial enlarged diagram of part F in FIG. 4.
Figure 9:
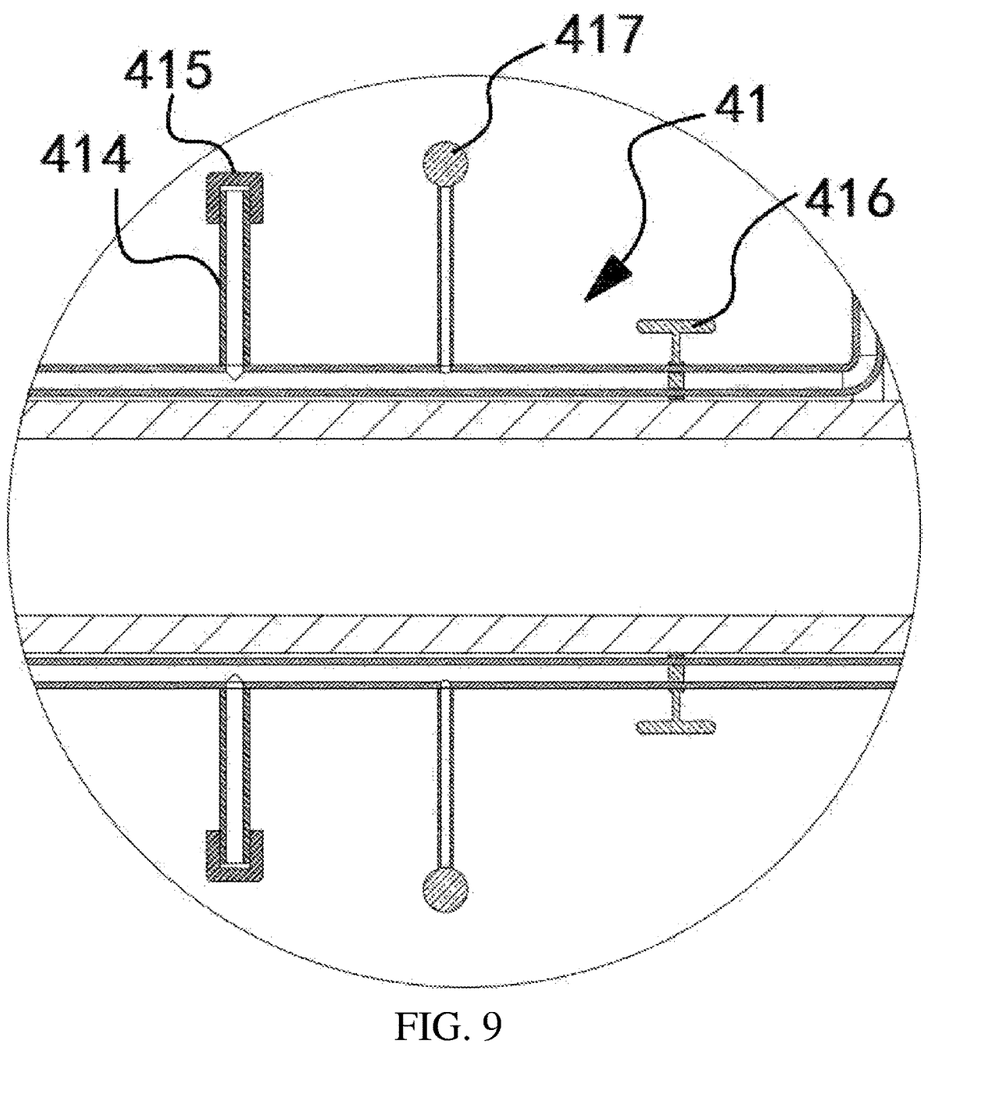
FIG. 9 is a partial enlarged diagram of part F in FIG. 4.
Figure 10:
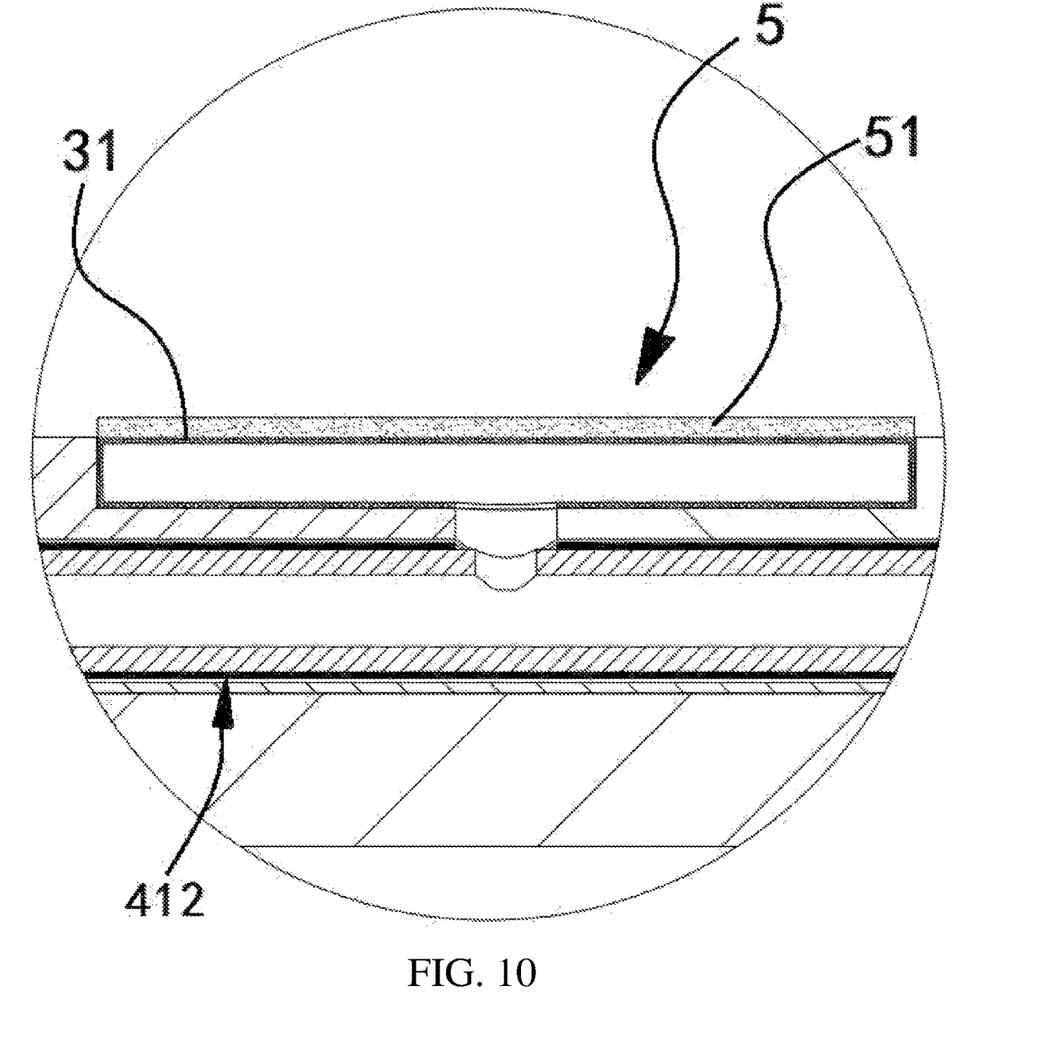
FIG. 10 is a schematic structural diagram of a flexible airbag during light-transmission detection.
Figure 11:
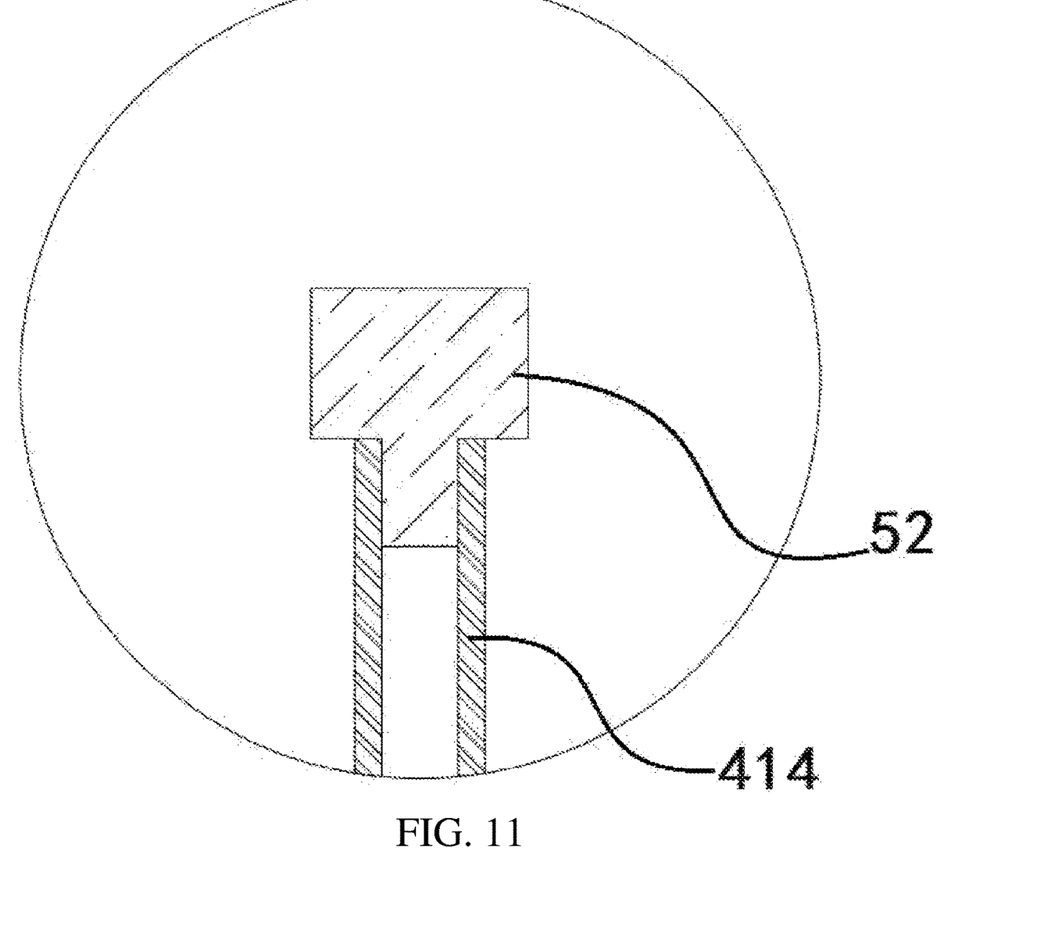
FIG. 11 is a schematic structural diagram of a light detection element during light-transmission detection.

Furthermore, the elastic airbag 31 is made of a translucent material. The confocal endoscope with a fixing device further includes a detector assembly 5. The detector assembly 5 includes at least one luminescent layer 51 and a light detection element 52. The luminescent layer 51 is selectively disposed on one or more elastic airbags 31, and the light detection element 52 is configured to detect whether there is light emitted by the luminescent layer 51 in the conveying tube 411.

The elastic airbag 31 may be made of various elastic transparent materials. Specifically, the elastic airbag 31 is made of elastic transparent rubber, but the material of the elastic airbag 31 is not limited thereto.

The material of the luminescent layer 51 may be a fluorescent agent, a photoluminescent material, or even a light-emitting diode, etc., and the light detection element 52 may be a light detection instrument composed of a fluorescence spectrometer, a photoresistor, or the like.

The specific work flow of the present invention is as follows: when it is necessary to detect the stomach and intestines of a human body through a confocal endoscope, first roughly presetting the detected site, selecting an appropriate insertion distance, and then selecting the number of elastic airbags 31 to be set as required, rotating the seal cartridges 4121 on the conveying tube 411, so that the seal cartridges 4121 seal some of the second communicating holes of the conveying tube 411, and then inserting one end of the conveying tube 411 into the fixing hole, so that the second communicating holes in the open state correspond to the positions of the elastic airbags 31 to be used, and the insertion depth and direction of the conveying tube 411 may be controlled; when the fixing tube is inserted the fixing hole, first roughly inserting to a suitable length, and then painting outer walls of the elastic airbags 31 to be opened with a luminous material, and detecting the inside of the conveying tube 411 through a detection element; detecting whether there is light emitted by the luminous layer 51 in the conveying tube 411; if light is detected, indicating that the elastic airbags 31 and the delivery tube 411 are in a connected state, and if light is not detected, indicating that the elastic airbags 31 are not communicated with the conveying tube 411, and adjusting the insertion depth and the circumferential angle of the conveying tube 411. The degree of opening can also be determined according to the intensity of the detected light.

When the fixing tube is in a proper position and is in a connected state through an optical path of the light detection element 52, the luminous layer 51 outside the elastic airbags 31 is removed, the pressure supply element 42 is activated, gas with a certain pressure is injected into the conveying tube 411, and the degree of opening of each elastic airbags 31 is tested, when there is no problem with the inflation of the elastic airbags 31, the cover body 415 is removed, the pressure is released through the branch tube 414, the gas in the elastic airbags 31 is discharged, and the elastic airbags 31 are retracted into the containing groove, then the insertion tube 1 and the flexible tube 2 are inserted into the to-be-detected part of the human body. When the lens on the insertion tube 1 is about to reach the predetermined location, the pressure supply element 42 is activated, and the pressure supply element 42 pumps the gas into the conveying tube 411, and the gas enters the elastic airbags 31 sequentially through the second communicating hole, the third communicating hole, the first communicating hole and the fourth communicating hole. Under the pressure of the gas, the elastic airbags 31 are continuously stretched, so that the elastic airbags 31 are abutted against the human body. The air pressure in the conveying tube 411 is constantly detected by the air pressure gauge, to avoid the pressure on the human body caused by the excessive air pressure in the conveying tube 411, and reduce the discomfort caused by the elastic airbags 31 to the human body. When the air pressure reaches a certain value, the air pressure in the conveying tube 411 is maintained. In this case, under the action of the elastic airbags 31, the elastic airbags 31 limit the flexible tube 2 and the insertion tube 1, and then move the insertion tube 1 to detect the intestinal tract, and the detected image is transmitted to an external image device through a pipeline harness for display.

After the detection, the pressure is released through the branch tube 414, the gas in the elastic airbags 31 is discharged, the elastic airbags 31 are retracted into the containing grooves, and then the insertion tube 1 is inserted, and the insertion tube 1 takes the flexible tube 2 out, and the detection is completed.

The specific implementations above of the present invention do not constitute a limitation to the protection scope of the present invention. Any other corresponding changes and modifications made according to the technical concept of the present invention shall be included in the protection scope of the claims of the present invention.

The invention claimed is:

1. A confocal endoscope with a fixing device, comprising:
    an insertion tube;
    a flexible tube, slidably sleeved outside the insertion tube, wherein a plurality of containing units are formed in an outer wall of the flexible tube in an axial direction and are distributed in the axial direction of the flexible tube at intervals, each containing unit comprises a plurality of containing grooves evenly distributed in a circumferential direction of the flexible tube, and the outer wall of the flexible tube is concaved inwards to form the containing grooves;
a plurality of airbag assemblies, wherein the airbag assemblies and the containing units are arranged in a one-to-one correspondence mode, each airbag assembly comprises a plurality of elastic airbags, the elastic airbags and the containing grooves are arranged in a one-to-one correspondence mode, and the elastic airbags are connected to inner walls of the containing grooves; and
a pressure supply assembly, selectively communicated with the elastic airbags of one or more airbag assemblies and configured to inject fluid media into the elastic airbags, wherein the elastic airbags are bulged to limit the flexible tube and restrain the insertion tube;
wherein
a plurality of fixing holes are formed on the flexible tube and are arranged in the axial direction of the flexible tube;
inner walls of the containing grooves are concaved inwards to form first communicating holes;
the first communicating holes are communicated with the fixing holes, and the elastic airbags are communicated with the first communicating holes;
the pressure supply assembly comprises a plurality of conveying elements and pressure supply elements;
the conveying elements and the fixing holes are arranged in a one-to-one correspondence mode;
each conveying element comprises a conveying tube and a sealing portion;
the conveying tube is slidably inserted in the fixing hole and is sealedly connected to an inner wall of the fixing hole;
second communicating holes opposite to the first communicating holes are formed on the conveying tube;
the second communicating holes and the first communicating holes are arranged in a one-to-one correspondence mode;
the sealing portion selectively seals some of the second communicating holes; and
the pressure supply element is communicated with each conveying tube and configured to inject fluid media into the conveying tube.

2. The confocal endoscope with a fixing device according to claim 1, wherein a plurality of annular grooves are formed on the conveying tube and are distributed in an axial direction of the conveying tube at intervals; the annular grooves are provided at both sides of each second communicating hole; each conveying element further comprises a plurality of seal rings; the seal rings and the annular grooves are arranged in a one-to-one correspondence mode; and inner races of the seal rings are matingly inserted in the annular grooves, and outer races are slidably abutted against the inner walls of the fixing holes and sealedly connected to the inner walls of the fixing holes.

3. The confocal endoscope with a fixing device according to claim 2, wherein the sealing portion comprises a plurality of seal cartridges; the seal cartridges and the second communicating holes are arranged in a one-to-one correspondence mode; the seal cartridges are rotatably sleeved on the conveying tube and sealedly connected to an outer wall of the conveying tube; two ends of each seal cartridge are abutted against two adjacent seal rings, respectively; and third communicating holes opposite to the second communicating holes are formed on the seal cartridge.

4. The confocal endoscope with a fixing device according to claim 3, wherein an outer diameter of the seal cartridge is smaller than that of the seal ring.

5. The confocal endoscope with a fixing device according to claim 2,
wherein a cross section of the annular groove is triangular;
wherein the seal ring comprises a first ring body and a second ring body, a cross section of the first ring body is triangular, and an inner race of the first ring body is matingly embedded in the annular groove; and
wherein the second ring body and the first ring body are coaxially arranged, an inner race of the second ring body is connected to an outer race of the first ring body, and the second ring body and the first ring body are integrally formed.

6. The confocal endoscope with a fixing device according to claim 1, wherein the elastic airbag is made of a translucent material; the confocal endoscope with a fixing device further comprises a detector assembly comprising at least one luminescent layer and a light detection element; the luminescent layer is selectively disposed on one or more elastic airbags, and the light detection element is configured to detect whether there is light emitted by the luminescent layer in the conveying tube.

7. The confocal endoscope with a fixing device according to claim 6, wherein the luminescent layer is made of a fluorescent agent, a photoluminescent material, or a light-emitting diode.

8. The confocal endoscope with a fixing device according to claim 6, wherein the light detection element is a light detection instrument composed of a fluorescence spectrometer and a photoresistor.

9. The confocal endoscope with a fixing device according to claim 1, wherein the flexible tube is made of flexible materials.

10. The confocal endoscope with a fixing device according to claim 9, wherein the flexible tube is made of medical silica gel.

11. The confocal endoscope with a fixing device according to claim 1, wherein a number of the containing grooves in each containing unit and a number of the elastic airbags in each airbag assembly are three, four or five.

12. The confocal endoscope with a fixing device according to claim 1, wherein a number of the fixing holes and the conveying elements is three, four or five.

13. The confocal endoscope with a fixing device according to claim 12, wherein the number of the fixing holes and the conveying elements is four, and the four conveying elements are evenly distributed along a circumferential direction of the conveying tube.

14. The confocal endoscope with a fixing device according to claim 1, wherein the fluid media comprise gas or liquid; the pressure supply element is an air pump in response to the gas, and the pressure supply element is a water pump in response to the liquid.

15. The confocal endoscope with a fixing device according to claim 1, wherein each conveying element further comprises a branch tube and a cover body; wherein an end of the branch tube is communicated with another end of the conveying tube, and external threads are provided on an outer wall of another end of the branch tube along an axial direction; wherein an inner wall of the cover body is hollow and an end is open, external threads are provided on the inner wall of the open end of the cover body along an axial direction, and the open end of the cover body is threadedly connected to the another end of the branch tube.

16. The confocal endoscope with a fixing device according to claim 1, wherein each conveying element further comprises a valve, and the valve is disposed on the conveying tube for controlling communication and closing of the conveying tube.

17. The confocal endoscope with a fixing device according to claim 1, wherein each conveying element further comprises an air pressure gauge, and the air pressure gauge is disposed at another end of the conveying tube for detecting air pressure in the conveying tube.

18. The confocal endoscope with a fixing device according to claim 1, wherein the elastic airbag is made of elastic transparent materials.

19. The confocal endoscope with a fixing device according to claim 18, wherein the elastic airbag is made of elastic transparent rubber.

* * * * *